United States Patent
Deisseroth

(10) Patent No.: US 10,046,041 B2
(45) Date of Patent: *Aug. 14, 2018

(54) **METHODS AND COMPOSITIONS FOR SUPPRESSING VIRULENCE OF METHICILLIN RESISTANT *STAPHYLOCOCCUS AUREUS***

(71) Applicant: MicroVAX, LLC, Warrenton, VA (US)

(72) Inventor: Albert B. Deisseroth, Potomac, MD (US)

(73) Assignee: MicroVAX, LLC, Warrenton, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/387,885

(22) Filed: Dec. 22, 2016

(65) Prior Publication Data

US 2017/0182145 A1  Jun. 29, 2017

Related U.S. Application Data

(63) Continuation of application No. 14/690,889, filed on Apr. 20, 2015, now Pat. No. 9,526,774, which is a continuation-in-part of application No. 13/775,343, filed on Feb. 25, 2013, which is a continuation-in-part of application No. 13/469,351, filed on May 11, 2012, which is a continuation-in-part of application No. 11/593,458, filed on Nov. 6, 2006, now Pat. No. 9,533,036.

(60) Provisional application No. 61/506,207, filed on Jul. 11, 2011, provisional application No. 61/486,834, filed on May 17, 2011.

(51) Int. Cl.

| | |
|---|---|
| *A61K 9/00* | (2006.01) |
| *C07K 14/31* | (2006.01) |
| *C12N 9/50* | (2006.01) |
| *C07K 14/70* | (2006.01) |
| *A61K 39/085* | (2006.01) |
| *C07K 14/705* | (2006.01) |
| *C07K 14/74* | (2006.01) |
| *C12N 7/00* | (2006.01) |
| *A61K 39/00* | (2006.01) |

(52) U.S. Cl.
CPC .......... *A61K 39/085* (2013.01); *A61K 9/0019* (2013.01); *C07K 14/31* (2013.01); *C07K 14/70539* (2013.01); *C07K 14/70575* (2013.01); *C07K 14/70578* (2013.01); *C12N 7/00* (2013.01); *C12N 9/50* (2013.01); *C12Y 304/23* (2013.01); *A61K 2039/5258* (2013.01); *A61K 2039/53* (2013.01); *A61K 2039/54* (2013.01); *A61K 2039/545* (2013.01); *A61K 2039/57* (2013.01); *A61K 2039/575* (2013.01); *A61K 2039/6031* (2013.01); *C07K 2319/00* (2013.01); *C07K 2319/02* (2013.01); *C12N 2710/10043* (2013.01)

(58) Field of Classification Search
CPC ............ C07K 14/005; C07K 14/70578; C07K 2319/06; C07K 2319/33; C07K 14/4748; C12N 2710/10343; C12N 2710/20022; C12N 15/1135; C12N 15/86; C12N 2310/3125; A61K 2039/5256; A61K 2039/53; A61K 2039/6031; A61K 2039/545; A61K 2039/70; A61K 31/70; A61K 39/0011; A61K 39/0208; A61K 39/07; A61K 9/127

See application file for complete search history.

(56) References Cited

U.S. PATENT DOCUMENTS 9,526,774 B1 * 12/2016 Deisseroth ........... A61K 39/085

OTHER PUBLICATIONS

Houghten et al. (Vaccines, 1986, Edited by Fred Brown: Cold Spring Harbor Laboratory).*

* cited by examiner

*Primary Examiner* — Padmavathi Baskar
(74) *Attorney, Agent, or Firm* — Jacob Frank; Glenn Snyder

(57) ABSTRACT

The present invention is directed to methods of suppressing the virulence of one or more virulence antigenic factors of methicillin resistant *Staphylococcus aureus* (MRSA). Aspects of the invention include administering of an expression vector alone or in conjunction with a fusion protein. The expression vector has a transcription unit encoding a fusion protein composed of a virulence antigenic factor of MRSA attached through a linker to the aminoterminal end of the ecd CD40 ligand. The fusion protein is composed of a virulence antigenic factor of MRSA and CD40 ligand and has the ability to generate antibodies which prevents host cell infection by suppressing virulence functions of MRSA.

12 Claims, No Drawings

METHODS AND COMPOSITIONS FOR SUPPRESSING VIRULENCE OF METHICILLIN RESISTANT *STAPHYLOCOCCUS AUREUS*

CROSS-REFERENCE TO RELATED APPLICATIONS

This application is a continuation of U.S. patent application Ser. No. 14/690,889 filed on Apr. 20, 2015, which is a continuation-in-part of U.S. patent application Ser. No. 13/775,343 filed on Feb. 25, 2013, which in turn is a continuation-in-part of U.S. patent application Ser. No. 13/469,351 filed on May 11, 2012, which in turn is a continuation-in-part of U.S. patent application Ser. No. 11/593,458, filed on Nov. 6, 2006, each of which applications, including all figures and tables, is incorporated herein by reference in its entirety.

This application also claims benefit under 35 U.S.C. § 119(e) of U.S. Provisional Patent Application No. 61/486,834, filed on May 17, 2011 and U.S. Provisional Patent Application No. 61/506,207, filed on Jul. 11, 2011, via U.S. patent application Ser. No. 13/469,351, which claims priority to these two U.S. Provisional patent applications, which, including all their collective figures and tables, are incorporated herein by reference in their entireties.

FIELD OF THE INVENTION

The present invention relates generally to the field of antimicrobial prophylaxis. More specifically, it is directed to novel methods of suppressing the virulence antigenic factors of methicillin resistant *Staphylococcus aureus* (MRSA) using four MRSA antigens fused to the CD40 ligand.

BACKGROUND OF THE INVENTION

The following discussion of the background of the invention is merely provided to aid the reader in understanding the invention and is not admitted to describe or constitute prior art to the present invention.

*Staphylococcus aureus*, a commensal microorganism that typically colonizes the anterior nares of 30% of the human population, is the leading cause of bacterial infections in the US. *Staphylococcus aureus* is a versatile pathogen that can express an array of virulence factors, including adhesins [e.g. fibronectin binding proteins (FnBPs) and protein A] that mediate binding to host cells, enzymes (e.g. proteases and lipases), toxins [e.g. alpha-haemolysin and Panton-Valentine leukocidin (PVL)], phenol-soluble modulins and capsular polysaccharides. Expression of these virulence factors is controlled by complex *staphylococcal* regulatory networks, including the accessory gene regulator (agr) system, and these genes vary between strains. Methicillin resistance in *S. aureus* results from acquisition of the mecA gene located within the mobile element known as the *staphylococcal* cassette chromosome mec (SCCmec). Until recently, eight SCCmec types were defined according to the SCCmec type and the chromosomal background determined by multilocus sequence typing.

*Staphylococcus aureus* strains have developed resistance to numerous antibiotics while MRSA, which have developed resistance to most if not all available antibiotic therapy, are very prevalent in hospitals in the US. These antibiotic resistant strains of MRSA also contain a number of proteins that are associated with the clinical virulence of these MRSA strains.

Methicillin resistant *Staphylococcus aureus* (MRSA) emerged in hospitals in the 1960s and is now the leading cause of hospital-associated infections. This hospital- or healthcare-associated MRSA (HA-MRSA) infection occur in individuals with risk factors for infection (e.g., surgery patients or immunocompromised patients). In contrast, community-associated MRSA (CA-MRSA) infections, first reported in the 1990s, occur in individuals without antecedent healthcare exposure or without such risk factors. Since the sixth decade of the 20$^{th}$ century, hospital and community acquired *Staphylococcus aureus* resistant infections have been noted in the following groups which are now considered high risk for infections of this organism which display resistance to multiple antibiotics: patients who are post-surgery or are in intensive care units or are in emergency rooms of hospitals, household contacts of individuals with antibiotic resistant *Staphylococcus aureus*, and individuals who are compromised in their ability to mount an immune response (innate or adaptive) against invasive infectious organisms: the very young (1), the very old, individuals with HIV or cystic fibrosis, institutionalized persons (nursing homes, military barracks, prisons), or individuals in underserved communities. Millions of cases of clinically significant infections of invasive strains of *Staphylococcus aureus* occur per year in the United States with over 100,000 deaths per year (2). In the beginning, the organisms responsible for these infections were only resistant to methicillin, but more recently, resistance to other antibiotics have been noted (clindamycin, vancomycin, daptomycin, mupirocin).

*S. aureus* has numerous cell surface proteins and secreted toxins that contribute to virulence by promoting evasion of the host innate immune system. In the past few years, the MSA300 strain has risen from 5% to a position of 42% of isolates in the United States, overtaking USA400 (3) and displacing other strains (ST30, ST80, ST93, and ST50). Many of these strains carry one or more of the following virulence factors:

1. Enterotoxins such as sek2 and seq2 (4);
2. The exotoxin proteins such as hemolysin A, which form pores in the membranes of cells by oligomerization, thereby disrupting the integrity of pulmonary vascular endothelial cells and alveolar cells (5-10). These exotoxins cause necrotizing pneumonia and lysis of leukocytes;
3. Protein A, which is a protein on the surface of *Staphylococcus aureus*, which inhibits opsonization or uptake of *Staphylococcus aureus* by phagocytes and promotes inflammation (7, 11-13);
4. Coagulases, which promote the walling-off of pockets of infectious organisms to generate abscesses (14-15);
5. *Staphylococcal* proteins which provide metabolic functions contributing to the phenotype of virulence in mouse models (such as the heme uptake protein IsdB) (16).

Given the rise of virulent organisms which display antibiotic resistance, the goal of development of MRSA vaccines for high risk populations has emerged as an important priority, which unfortunately has not yet been realized.

One factor that could prevent the success of vaccination is that the patients who are admitted to hospitals are often of advanced chronological age, are debilitated and/or immunosuppressed by the presence of chronic disease (17-20). These patients often do not respond to vaccination due to the diminished expression of CD40L in the CD40L helper T cells of these people (21-22). Another problem is that passive immunotherapy with opsonizing antibodies does not completely protect individuals against MRSA.

DETAILED DESCRIPTION OF THE INVENTION

In this specification, although the preferred embodiments have been described in detail, it should be understood that various changes, substitutions and alterations may be made therein without departing from the spirit and scope of the invention. Therefore, the specification is to be regarded in an illustrative rather than a restrictive sense.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in a suitable order unless otherwise indicated herein or otherwise clearly contradicted by context.

As used herein, the term "antigen" refers broadly to any antigen or portion thereof to which a human, mammal, bird or other animal can generate an immune response. "Antigen" as used herein refers broadly to a molecule that contains at least one antigenic determinant to which the immune response may be directed. The immune response may be cell-mediated, humoral or both.

As used herein, "antigenic determinant" refers to a single antigenic site or epitope on a complex antigenic molecule or particle, a minimal portion of a molecule that interacts with an antibody or T cell receptor. Antigenic determinants may be linear or discontinuous.

"Pharmaceutically acceptable" in the context of the present invention means a pharmaceutical composition that is generally safe, non-toxic and biologically acceptable for veterinary and human pharmaceutical use. Preferred compositions of this invention are intended for humans or animals.

The phrase "an effective amount" in reference to administering the fusion protein or an expression vector encoding that protein, is an amount that results in an increase in the immune response as measured by an increase in T cell activity or antibody production.

The fusion protein recited herein may be formulated with an adjuvant to enhance the resulting immune response. As used herein, the term "adjuvant" in the context of the instant invention means a chemical that, when administered with the expression vector or the fusion protein, enhances the immune response. An adjuvant is distinguished from a carrier protein in that the adjuvant is not chemically coupled to the antigen. Adjuvants are well known in the art and include, but not limited to, mineral oil emulsions (U.S. Pat. No. 4,608,251) such as Freund's complete or Freund's incomplete adjuvant (Freund, *Adv. Tuberc. Res.* 7:130 (1956); Calbiochem, San Diego Calif.), aluminum salts, especially aluminum hydroxide or ALHYDROGEL (approved for use in humans by the U.S. Food and Drug Administration), muramyl dipeptide (MDP) and its analogs such as [Thr$^1$]-MDP (Byersand Allison, *Vaccine* 5:223 (1987)), monophosphoryl lipid A (Johnson et al., *Rev. Infect. Dis.* 9:S512 (198)), and the like.

The term "vector" which contains a transcription unit (aka the "expression vector") as used herein refers to viral and non-viral expression vectors that when administered in vivo can enter target cells and express an encoded protein. Viral vectors suitable for delivery in vivo and expression of an exogenous protein are well known and include adenoviral vectors, adeno-associated viral vectors, retroviral vectors, vaccinia vectors, pox vectors, herpes simplex viral vectors, and the like. Viral vectors are preferably made replication defective in normal cells. For example, see U.S. Pat. Nos. 6,669,942; 6,566,128; 6,794,188; 6,110, 744; 6,133,029. The vector can be administered parenterally, such as intravascularly, intravenously, intra-arterially, intramuscularly, subcutaneously, or the like. Administration can also be orally, nasally, rectally, transdermally or aerosol inhalation. The vectors may be administered as a bolus, or slowly infused. The vector is preferably administered subcutaneously.

The term "transcription unit" as it is used herein in connection with an expression vector means a stretch of DNA that is transcribed as a single, continuous mRNA strand by RNA polymerase, and includes the signals for initiation and termination of transcription. For example, in one embodiment, a transcription unit of the invention includes nucleic acid that encodes from 5' to 3' a secretory signal sequence, an influenza antigen and CD40 ligand. The transcription unit is in operable linkage with transcriptional and/or translational expression control elements such as a promoter and optionally any upstream or downstream enhancer element(s). A useful promoter/enhancer is the cytomegalovirus (CMV) immediate-early promoter/enhancer. See U.S. Pat. Nos. 5,849,522 and 6,218,140.

The term "CD40 ligand" (CD40L) as used herein refers to a full length or portion of the molecule known also as CD154 or TNF5. CD40L is a type II membrane polypeptide having a cytoplasmic domain at its N-terminus, a transmembrane region and then an extracellular domain (ecd) at its C-terminus. Unless otherwise indicated the full length CD40L is designated herein as "CD40L," "wtCD40L" or "wtTmCD40L." The nucleotide and amino acid sequence of CD40L from mouse and human is well known in the art and can be found, for example, in U.S. Pat. No. 5,962,406. Also, included within the meaning of CD40 ligand are variations in the sequence including, but not limited to, conservative amino acid changes and the like which do not alter the ability of the ligand to elicit an immune response in conjunction with the fusion protein of the invention.

The term "neutralizing antibody" as used herein refers to antibodies that reduce the virulence, infectivity or pathogenicity of MRSA by partial or complete destruction of one or more MRSA virulence antigenic factor. The term "opsonizing antibody" as used herein refers to antibodies that bind to a receptor on MRSA and "mark" it for subsequent ingestion and destruction via phagocytes such as macrophage. In this context, an opsonizing antibody attaches to one or more MRSA virulence antigenic factors and acts as a binding enhancer for MRSA phagocytosis.

Some of the abbreviations used herein include: "Ad" (adenoviral); "sig" (signal sequence); "TAA" (target associated antigen); "ET" (epitope target); "ecd" (extracellular domain); and "sc" (subcutaneous).

The inventor's laboratory (23-31) has developed a TAA/ecdCD40L vaccine platform that is specifically designed to overcome the defective response to vaccination in immunosuppressed, debilitated patients who are of advanced chronological age. One of the reasons for the success of this platform is that it supplies a potent immunostimulatory signal (ecdCD40L) that is missing in older people. The presence of the TAA/ecdCD40L activates the DCs, as well as the antigen specific B cells and T cells, increases the potency of the vaccine, and directs the TAA along a Class I as well as a Class II MHC presentation pathway within the DC (21-22). This vaccination can be given subcutaneously as a TAA/ecdCD40L protein, as a subcutaneous injection of the Ad-sig-TAA/ecdCD40L vector, as an intramuscular injection of a DNA plasmid expression vector encoding the TAA/ecdCD40L protein, or as a subcutaneous injection of the fusion protein itself (23-31).

According to the invention, four DNA plasmid expression vector compositions against targets in MRSA were created as follows:

1. An expression vector carrying the Hla/ecdCD40L transcription unit and/or the Hla/ecdCD40L fusion protein itself. Hla is a 293 amino acid 33,400 kDa protein (32) the expression of which correlates with virulence (5-10, 33-34). The secreted HLA binds to the outer surface of the plasma membrane of target cells such as lymphocytes, macrophages, alveolar epithelial cells, pulmonary endothelial cells and erythrocytes (5-10). The Hla then oligomerizes into a heptameric prepore which inserts itself into the plasma membrane and increases the porosity thereby leading to death of the cells (5-10, 33-34). Hla expression is an essential virulence factor that contributes to mortality in lung infection (necrotizing pneumonia associated with alveolar epithelial cell damage and infiltration of white cells into the lung) in mouse models (10).

A mutant form of Hla, which is designated Hla$_H$35$_L$, contains a single amino acid substitution which replaces histidine with leucine at amino acid 35 position, thereby totally inactivating Hla as a pore forming lysin, presumably through loss of the ability of Hla monomers assembling themselves into hexamers to form the pore channel (35). This critical nature of the histidine at amino acid position 35 in the wild type protein suggests that neutralizing antibodies which bind to this location would block oligomerization and thereby abolish the virulence of the MRSA. We are proposing to attach a fragment of the wild type Hla, which contains the aminoterminal 45 amino acids, specifically:

(SEQ ID NO: 1)
ADSDINIKTGTTDIGSNTTVKTGDLVTYDKENGMHKKVFYSFIDD, to the amino terminal ecdCD40L (32). Antibodies to the Hla protein decrease virulence and the passive administration of these anti-Hla antibodies protects mice from lethal challenge (10).

2. An expression vector carrying the IsdB/ecdCD40L transcription unit and/or the IsdB/ecdCD40L fusion protein itself. IsdB is an iron regulated surface determinant (36). It is overexpressed on the surface of S. aureus under conditions of low iron concentration (16, 36-38). Its expression is suppressed at high iron concentrations. IsdB binds to hemoglobin thereby subserving a scavenging function for iron from host derived heme (36-38). Antibodies against IsdB can be found in the serum of normal individuals (38). Passive administration of such antibodies can confer protection in mice against lethal doses of S. aureus which is mediated in part by opsonophagocytic properties of these antibodies (36-39).

The fragment sequence from IsdB that has been selected for attachment to the amino terminal of ecdCD40L is shown as:

(SEQ ID NO: 2)
LNQLELREAIKNPAIKDKDHSAPNSRPIDFEMKKKDGTQQFYHYASSVKP

ARVIFT, which contains amino acids 125-183 of the IsdB protein (40). This fragment contains the first NEAr transporter 1 domain (NEAT 1), which is the initial binding site for hemoglobin to IsdB (40). This fragment also contains phenylalanine 164 (F164) which is also important for hemoglobin binding and also important for the rapid transfer of heme iron from hemoglobin to IsdB (40). Antibodies to this region are predicted on this basis to block the initial two steps of the process which allows uptake of heme iron into MRSA: 1. Binding of hemoglobin to NEAT 1 of IsdB, and 2. Transfer of heme iron from hemoglobin once bound to IsdB (40).

3. An expression vector carrying the SpA/ecdCD40L transcription unit and/or the SpA/ecdCD40L fusion protein itself (SpA is an abbreviation for a fragment of the *Staphylococcus aureus* Protein A. SpA binding to the Fcgamma of IgG antibodies interferes with opsonophagocytic clearance of S. aureus by polymorphonuclear leukocytes (11-13, 41). A 61 amino acid fragment of the D domain of Protein A was selected (42) for attachment to the amino terminal of ecdCD40L. This fragment has the following amino acid sequence:

(SEQ ID NO: 3)
ADAQQNNFNKDQQSAFYEILNMPNLNEAQRNGFIQSLKDDPSQSTNVLGE

AKKLNESQAPK

Neutralizing antibodies to this mutant Protein A block the immunoglobulin binding activities of SpA (11-13, 41-42). Antibodies specific to this protein protect mice from a challenge with a lethal dose of S. aureus (11-13, 41-42).

4. An expression vector carrying the Coag/ecdCD40L transcription unit and/or the Coag/ecdCD40L fusion protein itself. The TAA from S. aureus coagulase (43) which is to be connected to the amino terminal of ecdCD40L is composed of the following 41 amino acid fragment of coagulase:

(SEQ ID NO: 4)
MKKQIISLGALAVASSLFTWDNKADAIVTKDYSKESRVNEN

This sequence (43) is composed of a 26 amino acid signal sequence which is identical among all serotypes (43-44). Next are the first 7 amino acids of the secreted mature form of staphylocoagulase which also are identical among all serotypes. Crystallographic studies of the complex between prothrombin with staphylocoagulaase has shown that the first 7 amino acids which follow the signal sequence is the activating domain which is inserted into the activation pocket of prothrombin 2 thereby inducing an allosteric transformation to the active form, and triggering the formation of a clot (43). These first 30 amino acids are identical between the S. aureus Newman coagulase and the S. aureus von Willebrand binding protein coagulases.

The N-terminal domain of these two S. aureus coagulases bind to prothrombin inserting their N-terminal end into the catalytic pocket of the prothrombin, thereby activating it to trigger the conversion of fibrinogen to fibrin (43-45). This leads to a clot which encapsulates the abscess, thereby protecting the S. aureus from the host immune response.

Antibodies to these two proteins block this activation of clotting which leads to diminished virulence (15, 46).

In each case, the cDNA for a fragment encoding the epitope target (ET=Hla, IsdB, SpA, Coag) for each of the protective antibodies described above were attached via a cDNA encoding an 8-10 amino acid linker to a third cDNA attached to the aminoterminal end of the extracellular domain (ecd) of the murine CD40L. The four fragments were selected using the following criteria:

(i) selecting a fragment size of each of the four antigens small enough so that the ecdCD40L trimeric structure is not disrupted by attachment to the TAA;

(ii) selecting a fragment that is recognized and bound by MHC Class I;

(iii) selecting a fragment that is recognized and bound by MHC Class II;

(iv) selecting a fragment of each of 4 different virulence functions of MRSA which are on the surface of MRSA and which subserve a critical functional role in virulence which destroys the virulence of MRSA if lost from the bacterial cell wall; and (v) by providing at least four fragments which include fragments from four different antigens it reduces the probability of immunological escape due to mutational change.

This cDNA, encoding a secretable ET/ecdCD40L protein, is inserted into an expression vector (plasmid DNA or adenoviral).

Advantages of the ET/ecdCD40L Vaccine:

The instant invention creates a vaccine which prevents infection by disabling the virulence functions of MRSA. This vaccine is a pre-emptive preventative strategy employing a potent CD40L delivery platform that is applicable for wide use in the US population.

Background on Poor Response to Vaccine Among Older Individuals

In general, the response to vaccination may be limited by several factors: low immunogenicity of the target antigen, the state of health and the age of the individual, chronic infections or cancer, or other host factors which lead to defective function of CD8 T cells, CD4 T cells, B cells, and dendritic cells. The instant inventor has discovered that the linkage of the target antigen or a piece of the target antigen to the extracellular domain (ecd) of the CD40L at its aminoterminal end results in a dramatic increase in the magnitude of the immune response to the vaccine in young as well as older test subjects. This strategy converts weak antigens into strong and potent immunogens, and thereby overcomes states of anergy due to central or peripheral tolerance. This is due to the fact that the engagement of the CD40 receptor on antigen-specific B and CD8 T cells by the carboxyl terminal end of the CD40L on the surface of CD4 helper T cells is an essential step for these cells to expand in number in response to vaccination. For example, in older individuals, the absence of the presentation of the CD40L on activated CD4 helper T cells reduces the magnitude of the immune response to influenza vaccination. Recent analyses of human influenza vaccination clinical data show that less than 20% of individuals above 55 years of age develop a fully protective neutralizing antibody response to the yearly multivalent particle inactivated human influenza vaccine (17-20). This is due to the acquisition of both quantitative as well as qualitative defects such as loss of expression of CD40 ligand (CD40L) on CD4 helper T cells during activation (21) in the immune response as individuals reach the $5^{th}$ and $6^{th}$ decades of life. The TAA/ecdCD40L vaccine strategy overcomes this obstacle.

The Linker

The term "linker" as used employed in this application with respect to the transcription unit of the expression vector refers to one or more amino acid residues between the carboxy terminal end of the antigen and the amino terminal end of the CD40 ligand. The composition and length of the linker may be determined in accordance with methods well known in the art and may be tested for efficacy. (See, e.g. Arai et al. *Protein Engineering*, Vol. 4, No. 8, 529-532, August 2001). In certain embodiments of the present invention, the linker is generally from about 3 to about 15 amino acids long, more preferably about 5 to about 10 amino acids long. However, longer or shorter linkers may be used or the linker may be dispensed with entirely. Longer linkers may be up to about 50 amino acids, or up to about 100 amino acids. One example of a linker well-known in the art is a 15 amino acid linker consisting of three repeats of four glycines and a serine (i.e., [Gly$_4$Ser$_3$]).

TAA/ecdCD40L Vaccine Platform

The TAA/ecdCD40L vaccine can dramatically increase the potency of the immune response in healthy subjects, as well as subjects in whom the function of CD4 helper T cells is defective and thereby circumvent the functional defects in the immune response that are acquired in such individuals, as well as increase the immunogenicity of target antigens (23-31). There are several versions of this vaccine: (a) one in which the TAA/ecdCD40L transcription unit is embedded in a replication incompetent adenoviral vector (Ad-sig-TAA/ecdCD40L) which is used as an initial priming injection, followed by two sc injections of the TAA/ecdCD40L protein; (b) one in which the vaccine consists solely of the TAA/ecdCD40L protein, and (c) one in which the transcription unit for the TAA/ecdCD40L protein is inserted into a plasmid DNA expression vector. The TAA is connected through the linker to the aminoterminal end of the extracellular domain (ecd) of the potent immunostimulatory signal CD40 ligand (CD40L). The attachment of the TAA to the CD40L accomplishes two things: (a) the binding of the TAA/ecdCD40L protein to the CD40 receptor on the dendritic cells (DCs) as well as on the B cells and T cells, activate these cells thereby replacing the CD40L signal which is missing on the plasma membrane of the CD4 helper T cells of older individuals (21-22); and (b) once the TAA/ecdCD40L protein is engaged on the CD40 receptor of the DC, the entire TAA/ecdCD40L protein is internalized into the DC in a way that allows the TAA to be processed through the Class I as well as the Class II MHC presentation pathways (23-31). The activated TAA loaded DC then migrate to the regional lymph nodes (24) where they can activate and induce expansion of the TAA specific CD8 effector T cells. These antigen specific CD8 effector cells become increased in number in the lymph nodes (23, 26), egress from the lymph nodes into the peripheral blood. The antigen specific CD8 effector T cells exit the intravascular compartment and enter into the extravascular sites of inflammation or infection. In addition to showing that this vaccine increases the antigen specific CD8 effector T cells in the sites of inflammation, we have shown that the activation and expansion of the B cells by the TAA/ecdCD40L protein increases the levels of the TAA specific antibodies in the serum (23-31).

Previous Work on Vaccine Strategies for MRSA

Four targets have been reported on *Staphylococcus aureus* which have successfully been used to elicit antibodies for the passive transfer of immunity to diminish the severity of infections of *Staphylococcus aureus* in 6-week old mice:

1. Hla Passive Antibody Administration: Protection against *Staphylococcus aureus* induced necrotizing pneumonia has been demonstrated in a C57BL/6 mouse model by Wardenburg and Schneewind (10) using passive antibody immunization against alpha-hemolysin (Hla). As mentioned above, Hla is a water soluble monomeric exotoxin secreted by *Staphylococcus aureus*, which binds to the plasma membrane where it oligomerizes into heptamers thereby creating pores in the membranes of pulmonary endothelial cells and alveolar epithelial cells. This causes lethal necrotizing pneumonia and pulmonary capillary vascular leak (5-10, 32-35).
2. Recombinant Vaccines Against IsdA and IsdB Induce Passive Immunity to *Staphylococcal aureus*: IsdB is a surface protein on *Staphylococcus aureus* which promotes uptake of heme scavenged from host hemoglobin. Kim et al. (16) have shown that the passive administration of antibodies against fragments of IsdB provide protection in 6 week old BALB/c mice for challenge by lethal doses of *Staphylococcus aureus* (16).
3. Passive Vaccination Against SpA (Protein A of *Staphylococcus Aureus*) Reduce Mortality in Test Mice. SpA is a *Staphylococcus aureus* protein that interferes with the process of uptake of *Staphylococcus aureus* by phagocytic cells mediated by opsonizing antibodies of the host (11-13, 41-42). Kim et al have shown that passive immunization of mice with antibodies to SpA reduced the mortality of lethal challenge doses of methicillin resistant *Staphylococcus aureus* (MRSA), and increased the efficiency of clearance of MRSA by opsonophagocytic mechanisms (11-13, 41-42).
4. Passive Immunization of Mice Against Coagulase Associated Epitopes. Coagulases promote walling-off of pockets of infection of *Staphylococcus aureus* which lead to protection of infectious organisms from the immune response and from antibiotics (14-15, 43-45). Passive administration of antibodies to various coagulase functions protected mice from formation of renal abscesses by USA300 *Staphylococcus aureus* strains (15).

Application of ecdCD40L Vaccine Platform to Influenza

The inventor's laboratory has previously demonstrated that the HA/ecdCD40L vaccine and the M2/ecdCD40L vaccine, where HA and M2 are derived from the A/Hong Kong/156/97 avian influenza virus, dramatically increases the levels of both HA and M2 specific splenic CD8 T cells as well as HA and M2 specific antibodies even in aged test mice (29). The levels of the response induced in old as well as young mice to avian M2, which is a weak immunogen, by the M2/ecdCD40L vaccine are equivalent to the levels of hemagglutinin (HA) specific CD8 T cells and serum antibodies induced by the HA/ecdCD40L vaccine (where HA is also derived from the A/Hong Kong/156/97 virus). The response to previous vaccines involving M2 flu antigens in a viral particle or as a recombinant protein is historically much weaker than to vaccines involving HA. Thus, it appears that the linkage of the M2 antigen to CD40L has not only overcome the defect in CD4 helper T cell function among older test subjects, but it has also dramatically increased the immunogenicity of weak viral antigens (29).

Innovative Approach for a *Staphylococcus Aureus* Vaccine

Passive immunization of mice with antibodies against the following proteins of *Staphylococcus aureus* listed above provided the first evidence that immunization can prevent or reduce the severity of MRSA infections in test mice: 1. coagulase (14-15, 43-45), 2. IsdB heme uptake protein (16,36-40), 3. alpha-hemolysin (5-10, 32-35), and protein A (11-13, 41-42). Merck has initiated clinical testing of a vaccine (V710) against the IsdA and IsdB heme uptake proteins in human subjects and shown initial evidence that the vaccine induces an adaptive immune response (46). However, the detection of antibodies to protein A and coagulase in uninfected individuals as well as in individuals with progressive MRSA infections (4) suggest that additional novel strategies may be necessary to provide protection against MRSA strains which elaborate multiple different types of virulence factors.

Another problem is that the patient populations at risk are often chronically ill, or are elderly, or have other conditions which lead to unresponsiveness to vaccination. As an example, in a study of 60,000 individuals vaccinated with the multi-valent particle inactivated influenza vaccine, only 20% of individuals above the age of 55 developed a fully protective neutralizing antibody response (17-20). This is due to the acquisition of qualitative defects CD4 helper T cell function in the elderly, such as loss of expression of CD40 ligand (CD40L) on CD4 helper T cells during activation (21-22).

This data suggests that future programs of vaccination should be comprised of mixtures of vaccines against the 4 virulence factors described above (hemolysin A, Protein A, IsdB and coagulase) and that the vaccine strategy can overcome the diminished response to vaccination that is seen in the chronically ill or the elderly (17-20). In order to overcome such obstacles, the inventor's laboratory (23-31) attached the target associated antigen (TAA) through a nine amino acid linker to the amino-terminus of the extracellular domain (ecd) of the potent immunostimulatory signal, the CD40 ligand (CD40L). This strategy has been studied three ways discussed below:

(a) one in which the TAA/ecdCD40L transcription unit preceded by a secretory signal (sig) is embedded in a replication incompetent adenoviral vector (Ad-sig-TAA/ecdCD40L) which is injected subcutaneously by itself;

(b) a second strategy in which the Ad-sig-TAA/ecdCD40L is used as an initial priming injection, followed by two sc injections of the TAA/ecdCD40L protein;

(c) a third strategy in which the vaccine consists solely of subcutaneous injections of the TAA/ecdCD40L protein. The TAA is connected through a linker to the ecd of the CD40L; and (d) a fourth strategy in which the vaccine consists of a plasmid expression vector which has a transcription unit which encodes the TAA/ecd/CD40L protein.

The attachment of the TAA to the amino terminal of ecdCD40L accomplishes two things: (a) promotes the CD40 receptor mediated uptake of the TAA into the dendritic cells so as to promote effective presentation of the TAA on class I and II MHC as well as activation of the secondary signals on the dendritic cells (23, 26), and (b) the provision of the CD40L signal (23, 26) which is missing on the CD4 helper T cells of older or chronically ill individuals (21-22). The activated TAA loaded DC then migrate to the regional lymph nodes (24) where they can activate and induce expansion of the TAA specific CD8 effector T cells. These antigen specific CD8 effector cells become increased in number in the lymph nodes (24), egress from the lymph nodes into the peripheral blood, and then accumulate (24, 26) at sites of inflammation (infection or tumor nodules). The TAA/ecdCD40L vaccine also increases the levels of the TAA specific antibodies in the serum (24, 26, 29-30). The TAA/ecdCD40L vaccine induces a memory response which persists for greater than 1 year (23). The attachment of weakly immunogenic antigens to the CD40L induces a robust cellular and humoral immune response even in the aged immune system (26, 29) and in states of lymphopenia (30).

According to one embodiment of the present invention, the TAA/ecdCD40L vaccine platform is used for the generation of a multi-valent DNA vaccine to induce an adaptive immune response against four of the virulence factors of MRSA for which the passive transfer of antibodies reduce the severity or prevent the infection of test mice with MRSA strains.

MRSA Vaccine Using the TAA/ecdCD40L Vaccine Platform

Four compositions were generated against MRSA protein targets, each containing a specific virulence antigenic factor:
1. The Hla/ecdCD40L protein;
2. The IsdB/ecdCD40L protein;
3. The SpA/ecdCD40L protein; and
4. the Coag/ecdCD40L protein.

In each case, the cDNA for a fragment encoding the epitope target (ET) described above comprising virulence antigen factors 1-4, may be attached through a 9 amino acid linker to the amino-terminus of the ecd of the murine CD40L. The cDNA encoding a secretable ET/ecdCD40L protein where E4=4 different virulence factors cited above was inserted into a plasmid expression system encoding the ET/ecdCD40L protein.

Accordingly, in one aspect, the invention provides a method of disabling the following 4 virulence antigenic factors of MRSA in an individual by administering an expression vector (selected from plasmid DNA or adenoviral vectors which carry transcription units encoding each of the following fusion proteins: Hla/ecdCD40L, Coag/ecdCD40L, SpA/ecdCD40L, IsdB/ecdCD40L) which contain a transcription unit encoding a secretable fusion protein that comprises a MRSA virulence antigenic factor and CD40 ligand, wherein said fusion protein has the ability to generate antibodies which prevent cell infection and suppress MRSA. In yet another embodiment of the instant invention, the method further comprises administering a fusion protein (comprising Hla/ecdCD40L, IsdB/ecdCD40L, Coag/ecdCD40L, SpA/ecdCD40L) which contains a MRSA virulence antigenic factor and CD40 ligand. In other embodiment of the present invention, pharmaceutical compositions containing one or more expression vector and/or fusion proteins for blocking the virulence of one or more virulence antigenic factors of MRSA are also provided.

Clearly, the instant invention provides a pre-emptive preventative strategy for the induction of a potent adaptive immune response against four key virulence factors of the MRSA. This strategy overcomes the potential problems associated with previous attempts at MRSA vaccination outlined above that has multiple virulence factors and populations of test subjects that have reduced responsiveness to vaccination due to advanced chronological age and/or anergy arising from chronic disease.

REFERENCES

1. Hersh A L, Shapiro D J, Newland J G, Polgreen P M, Beenmann S E, and Shah S S. Variability I pediatric infectious disease consultants recommendations for management of community-acquired pneumonia. PLoS ONE 6: e20325, 2011.
2. Klevens R M, Morrison M A, Nadle J, Petit S, Gershman K, Ray S, Harrison L H, Lynfield, R, Dumyati G, Townes J M, Craig A S, Zell E R, Fosheim G E, McDougal L K, Carey R B, Fridkin S K. Active bacterial core surveillance (ABCs) MRSA investigators. JAMA 298: 1763, 2007.
3. Mongkolrattanothai K, Boyle S, Kahana M D, and Daum R S. Severe *Staphylococcus aureus* infections caused by clonally related community-acquired methicillin-susceptible and methicillin-resistant isolates. Clinical Infectious Diseases 37: 1050-1058, 2003.
4. Dief B A, Gill S R, Chang R F, Phan T H, Chen J H, Davidson M G, Lin F, Lin J, Carleton H A, Mongodin E F, Sensabaugh G F, and Perdreau-Remington F. Complete genome sequence of USA 300, an epidemic clone of community-acquired methicillin-resistant *Staphylococcus aureus*. Lancet 367: 731-739, 2006.
5. Bubeck Wardenburg J, Bae T, Otto M, Deleo F R, Schneewind O. Poring over pores: alpha-hemolysin and Panton-Valentine leukocidin in *Staphylococcus aureus* pneumonia. Nature Medicine 13: 1405-1406, 2007.
6. Cheung A L, Bayer A S, Zhang G, Gresham H, and Xiong Y Q. Regulation of virulence determinants in vitro and in vivo in *Staphylococcus aureus*. FEMS Imunol Med Microbiol 40: 1-9, 2004.
7. David M Z, and Daum R S. Community-associated methicillin-resistant *Staphylococcus aureus*: epidemiology and clinical consequences of an emerging epidemic. Clinical Microbiology Reviews. 23: 616-687, 2010.
8. Song L, Hobaugh M R, Shustak C, Cheley S, Bayley H, and Gouaux J E. Structure of *Staphylococcal* alpha-hemolysin, a heptameric transmembrane pore. Science 274: 1859, 1996.
9. Kennedy A D, Bubeck Wardenburg J, Gardner D J, Long D, Whitney A R, Braughton K R, Schneewind O, DeLeo F R. Targeting of alpha or passive immunization decreases severity of USA300 skin infection in a mouse model. Journal of Infectious Disease 202: 1050-1058, 2010.
10. Bubeck Wardenburg J, and Schneewind O. Vaccine protection against *Staphylococcus aureus* pneumonia. J Exp Med 205: 287-294, 2008.
11. Uhlen M, Guss B, Nilsson B, Gatenbeck S, Philipson L, and Lindberg M. Complete sequence of the *staphylococcal* gene encoding protein A. Journal of Biological Chemistry 259: 1695-1702, 1984.
12. Foster T J. Immune evasion by *staphylococci*. Nat Rev Microbiol 3: 948-958, 2005.
13. Patel A H, Nowlon P, Weavers E D, and Foster T. Virulence of protein A-deficient and alpha-toxin-deficient mutants of *Staphylococcus aureus* isolated by allele replacement. Infect. Immun 55: 3103-3110, 1987.
14. Clarke S R, Brummell K J, Horsburgh M J, McDowell P W, Mohamad S A, Stapleton M R, Acevedo J, Read R C, Day N P, Peacock S J, Mond J J, Kokai-Kun J F, and Foster S J. Identification of in vivo-expressed antigens of *Staphylococcus aureus* and their use in vaccinations for protection against nasal carriage. J Infect Dis 193: 1098-1108, 2006.
15. Cheng A G, McAdow M, Kim H K, Bae T, Missiakes D M, and Schneewind O. Contribution of coagulases towards *Staphylococcus aureus* disease and protective immunity. PLoS Pathog 6: e1001036, 2010.
16. Kim H K, DeDent A, Cheng A G, McAdow M, Bahnoli F, Missiakas D M, and Schneewind O. IsDA and IsdB antibodies protect mice against *Staphylococcus aureus* abscess formation and lethal challenge, Vaccine 28: 6382-6392, 2010.
17. Jefferson T, Rivetti D, Rivetti A, Rdin M, Di Pietrantonj C, and Demicheli V. Efficacy and effectiveness of influenza vaccines in elderly people: a systematic review. Lancet 366, 1165-1174, 2005.
18. Goodwin K, Viboud C, and Simonsen L. Antibody response to influenza vaccination in the elderly: a quantitative review. Vaccine 24, 1159-1169, 2006.
19. Simonsen L et al. Lancet Inf. Dis 7: 658-666, 2007.
20. Jackson M L et al., Lancet 372: 398-405, 2008.
21. Dong L, More I, Hossain J M, Liu B, and Kimjra Y. An immunostimulatory oligodeoxynucleotide containing a cytosine-guanosine motif protects senescence-accelerated mice from lethal influenza virus by augmenting the T helper type 1 response. Journal of General Virology 84, 1623-1628, 2003.
22. Eaton S M et al. J. Exp. Med. 200: 1613-1622, 2004.
23. Zhang L, Tang Y, and Deisseroth A. Adenoviral vectors encoding a secretable HPV 16 E7/CD40 ligand fusion protein induce immunity for up to one year in a murine model. PNAS, 100: 15101-15106, 2003.
24. Tang, Y, Zhang, L, Yuan, J, Maynard, J, and Deisseroth, A. Multi-step process of vector mediated activation and tumor antigen loading of APC by CD40 ligand/tumor antigen secretory protein generates protection from cancer cell lines. Blood, 104: 2704-2713, 2004.
25. Akubulut H, Tang Y C, Maynard J, and Deisseroth A. Dendritic cells improve the efficacy of vector targeted chemotherapy in breast cancer. Molecular Cancer Therapeutics 5: 1975-1985, 2006.
26. Tang, Y C, Maynard J, Akbulut H, Fang X M, Zhang W W, Xia X Q, Koziol J, Linton P J, and Deisseroth. Vector Prime/Protein Boost Vaccine Which Overcomes Defects Acquired During Aging and Cancer. J. Immunology, 177:5697-5707, 2006.
27. Tang Y, Akbulut H, Maynard J, Zhang L, Petersen L, and Deisseroth A. Vaccine strategies for cancer and infectious diseases in the elderly. Gene Therapy 2007, Edited by T. Ochiai, H. Shimada, and M. Tagawa, Chiba, Japan, pp. 78-85, 2007.
28. Akbulut H, Tang Y C, Maynard J, and Deisseroth A. Chemotherapy targeted to cancer tissue potentiates antigen specific immune response induced by vaccine for antigen loading and activation of dendritic cells. Molecular Therapy, 10: 1753-1760, 2008.
29. Tang, Y C, Linton, P J, Thoman M, and Deisseroth A. Symposium in Writing: Vaccine for Infections and Cancer. Cancer Immunology Immunotherapy 58: 1949-1957, 2009.
30. Han T H, Park Y H, Maynard J, Li P C, Tang Y C, and Deisseroth A. Ad-sig-BcrAbl/ecdCD40L Vector Prime-BcrAbl/ecdCD40L Protein Boost Vaccine for P210Bcr-Abl Protein, Bone Marrow Transplantation, 45: 550-557, 2010.
31. Akbulut H, Tang Y C, Akbulut G, Maynard J, and Deisseroth A. Vaccine combined with vector targeted chemotherapy reduces levels of cancer stem cells and improves outcome of cancer treatment, Gene Therapy 17: 1333-1340, 2010.
32. Gray G S, and Kehoe M. Primary sequence of the alpha-toxin gene from Staphylococcus aureus Wood 46. Infection and Immunity 46: 615-618, 1984.
33. Bhakdi S, and Tranum-Jensen J. Alpha-toxin of Staphylococcus aureus. Microbiological Reviews 55: 733-751, 1991.
34. Wardenburg J B, Patel R J, and Schneewind O. Surface proteins and exotoxins are required forte pathogenesis of Staphyloccus aureus pneumonia. Infection and Immunity 75: 1040-1044, 2007.
35. Menzies B E and Kernodle E}D S. Passive immunization with antiserum to non-toxic alha-toxin mutant from Staphyloccus aureus is protective in a murine model. Infection and Immunity 64: 1839-1841, 1996.
36. Kuklin N A, Clark D J, Secore S, Cook J, Cope L D, McNeely T et al. A novel Staphylococcus aureus vaccine. Infection and Immunity 74: 2215-2223, 2006.
37. Kim H K, DeDent A, Cheng A G, McAdow M, Bagnoli F, Missiakas D M, and Schneewind O. IsdA and IsdB antibodies protect mice against Staphylococcs aureus abscess formation and lethal challenge. Vaccine 28: 6382-6392, 2010.
38. Mazmanian S K, Skaar E P, Gaspar A H, Humayun M, Gornicki P, Jelenska J, Joachmiak A, Missiakas D M, and Schneewind O. Passage of heme-iron across the envelope of Staphyococcus aureus. Science 299: 906-909, 2003.
39. Stranger-Jones Y K, Bae T, and Schneewind O. Vaccine assembly from surface proteins of Staphylococcus aureus. PNAS 103: 16942-16947, 2006.
40. Fonner B A, Tripet B P, Eilers B J, Stanisich J, Sullivan-Springhetti R K, Moore R, Li M, Lei B, and Copie V. Solutiion structure and molecular determinants of hemoglobin binding of the first NEAT domain of IsdB in Stapylococcus aureus. Biochemistry 53: 3922-3933, 2014.
41. Kim H K, Emolo C, DeDent A C, Falugi F, Missiakas D M, and Schneewind O. Protein A-specific monoclonal antibodies and prevention of Staphylococcus aureus disease in mice. Infection and Immunity 80: 3460-3470, 2012.
42. Kim H K, Cheng A G, Kim H Y, Missiakas D M, and Schneewind O. Nontoxigenic protein A vaccine for methicilliin-resistant Staphylococcus aureus infections in mice. JEM 207: 1863-1870, 2010.
43. Watanabe S, Ito T, Takeuchi F, Endo M, Okuno E, and Hiramatsu K. Structural comparison of ten serotypes of Staphylocoagulases in Staphylococcus aureus. Journal of Bacteriology 187: 3698-3707, 2005.
44. Friedrich R, Panizzi P, Fuentes-Prior P, Richter K, Verhamme I, Anderson P J, Kawabata S I, Huber R, Bode W, and Bock P E. Staphylocoagulase is a prototype for the mechanism of cofactor-induced zymogen activation. Nature 425: 535-539, 2003.
45. McAdow M, Kimm H K, DeDent A C, Hendrickx A P A, Schneewind O, and Missiakas D M. PLoS Pathogens 7: e1002307, 2011.
46. Harro C, Betts R, Olrensteikn W, Kwak E J, Greenberg H E, Onorato M T, Jartzel J, Lipka J, DiNubile M J, and Kartsonis N. Safety and immunogenicity of a novel Staphylococcus aureus vaccine: results from the first study of the vaccine dose range in humans. Clin Vaccine Immunol 17: 1868-1874, 2010.

All references, including publications, patent applications, and patents, cited herein are incorporated by reference in full to the same extent as if each individual publication was specifically and individually indicated to be incorporated by reference. They are indicative of the levels of those of ordinary skill in the art to which the invention pertains and may be employed in the practice of the invention.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed.

Thus, it is understood that the invention is not limited to the disclosed methods, compositions and embodiments shown, including any embodiments that may be apparent to one of ordinary skill in the art. Although the foregoing invention has been described in some detail, it will be readily apparent to those of ordinary skill in the art in light of the teachings of this invention that certain variations and modifications may be made thereto without departing from the spirit or scope of the disclosure herein, including the specific embodiments. Other embodiments are set forth within the following claims.

I claim:

1. A pharmaceutical composition comprising a mixture of vectors for generating humoral and cellular immune response against methicillin resistant *Staphylococcus aureus* (MRSA) in an individual, each of said vectors comprising one of four transcription units each encoding a secretory signal sequence attached to a different one of four fusion proteins, each of said four fusion proteins comprising (i) a different one of four fragments, SEQ ID NOS 1-4, respectively from the extracellular domain of each of the four proteins Hla, IsdB, SpA and Coag, (ii) a secretable CD40 ligand, (iii) each of said peptide fragments having epitopes recognized and bound by both MHC Class I and MHC Class II, (iv) a separate linker connecting each of the said four fragments to an amino-terminal end of an extracellular domain of a secretable CD40 ligand and wherein said composition has the ability to promote antibody response for blocking the virulence of one or more virulence antigenic factors of MRSA.

2. The composition of claim 1, wherein said vectors are expression vectors.

3. The composition of claim 2, wherein said expression vectors are adenoviral expression vectors.

4. The composition of claim 2, wherein each of said expression vectors is a plasmid DNA or viral vector.

5. The composition of claim 1 wherein each of the transcription units encodes a secretory signal sequence.

6. The composition of claim 1, wherein said promotion of a humoral response is an antibody response is selected from the group consisting of neutralizing antibodies, opsonizing antibodies and a combination thereof.

7. A composition for increasing the immune responsiveness of an individual against multiple virulence antigenic factors of methicillin resistant *Staphylococcus aureus* (MRSA), comprising administering to the individual an effective amount of a composition comprising four plasmid DNA expression vectors each expression vector carrying a transcription unit encoding a secretory signal sequence attached to a different one of four distinct amino acid fragments, SEQ ID NOS 1-4 respectively from the protein group consisting of Hla, IsdB, SpA and Coag, wherein each of said four fragments is connected as a fusion protein to an amino-terminus of an extracellular domain of a CD40 ligand (ecdCD40ligand) having a trimeric structure, each of said four fragments of an amino acid size sufficiently small so that the trimeric structure of the ecdCD40 ligand is not disrupted, and wherein said composition has the ability to generate MHC Class I and Class II cytotoxic T cells and antibodies, which help prevent cell infection by MRSA.

8. A composition according to claim 7, wherein said antibodies are neutralizing antibodies.

9. A method of inducing an immune response against *Staphylococcus aureus* (MRSA) in a subject comprising administering to said subject an effective amount of the immunogenic composition of claim 1.

10. The method of claim 9, wherein said CD40 ligand is human CD40 ligand and said humoral response is an inducement of neutralizing antibodies.

11. The method of claim 9, wherein said fusion proteins or vectors encoding said fusion proteins are administered with one or more adjuvants.

12. The method of claim 9, wherein said fusion proteins are subcutaneously administered as a single dose or as multiple doses.

* * * * *

```
                       SEQUENCE LISTING

<160> NUMBER OF SEQ ID NOS: 4

<210> SEQ ID NO 1
<211> LENGTH: 45
<212> TYPE: PRT
<213> ORGANISM: Artificial Sequence
<220> FEATURE:
<223> OTHER INFORMATION: Synthetic Construct

<400> SEQUENCE: 1

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp
        35                  40                  45

<210> SEQ ID NO 2
<211> LENGTH: 56
<212> TYPE: PRT
<213> ORGANISM: Artificial Sequence
<220> FEATURE:
<223> OTHER INFORMATION: Synthetic Construct

<400> SEQUENCE: 2

Leu Asn Gln Leu Glu Leu Arg Glu Ala Ile Lys Asn Pro Ala Ile Lys
1               5                   10                  15

Asp Lys Asp His Ser Ala Pro Asn Ser Arg Pro Ile Asp Phe Glu Met
            20                  25                  30

Lys Lys Lys Asp Gly Thr Gln Gln Phe Tyr His Tyr Ala Ser Ser Val
        35                  40                  45

Lys Pro Ala Arg Val Ile Phe Thr
    50                  55

<210> SEQ ID NO 3
<211> LENGTH: 61
<212> TYPE: PRT
<213> ORGANISM: Artificial Sequence
<220> FEATURE:
<223> OTHER INFORMATION: Synthetic Contsruct

<400> SEQUENCE: 3

Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Ala Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60

<210> SEQ ID NO 4
<211> LENGTH: 41
```

```
<212> TYPE: PRT
<213> ORGANISM: Artificial Sequence
<220> FEATURE:
<223> OTHER INFORMATION: Synthetic Construct

<400> SEQUENCE: 4

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
            20                  25                  30

Ser Lys Glu Ser Arg Val Asn Glu Asn
            35                  40
```